United States Patent

Seelich

[11] Patent Number: 5,962,405
[45] Date of Patent: Oct. 5, 1999

[54] STORAGE-STABLE FIBRINOGEN PREPARATIONS

[75] Inventor: Thomas Seelich, Vienna, Austria

[73] Assignee: Immuno Aktiengesellschaft, Vienna, Austria

[21] Appl. No.: 08/838,975

[22] Filed: Apr. 23, 1997

[30] Foreign Application Priority Data

Apr. 30, 1996 [DE] Germany ............... 196 17 369

[51] Int. Cl.⁶ ............... A61K 38/00; C07K 5/00; C07K 7/00
[52] U.S. Cl. ............... 514/2; 530/382; 530/383; 424/101
[58] Field of Search ............... 530/382–383; 514/2; 424/101

[56] References Cited

U.S. PATENT DOCUMENTS

| | | | |
|---|---|---|---|
| 4,298,598 | 11/1981 | Schwarz et al. | 424/101 |
| 4,377,572 | 3/1983 | Schwarz et al. | 424/101 |
| 4,909,251 | 3/1990 | Seelich | 514/2 |
| 5,330,974 | 7/1994 | Pines et al. | 514/21 |

FOREIGN PATENT DOCUMENTS

| | | |
|---|---|---|
| 18306/92 | 6/1992 | Australia . |
| 359 652 | 2/1979 | Austria . |
| 359 653 | 2/1979 | Austria . |
| 369 990 | 2/1979 | Austria . |
| 371 719 | 7/1983 | Austria . |
| 0 085 923 | 8/1983 | European Pat. Off. . |
| 0 159 311 | 10/1985 | European Pat. Off. . |
| 0 315 222 | 5/1989 | European Pat. Off. . |
| 0 345 246 | 12/1989 | European Pat. Off. . |
| 0 455 626 | 11/1991 | European Pat. Off. . |
| 2 042 556 | 2/1979 | United Kingdom . |

OTHER PUBLICATIONS

L.A. Kazal et al., The Preparation and Some Properties of Fibrinogen Precipitated from Human Plasma by Glycine. *Proc. Soc. Exp. Biol. Med.* 113:989–994 (1963).

Redl et al. "Medizinische Welt" Abstract 36:769–776 (1985).

*Primary Examiner*—Avis M. Davenport
*Attorney, Agent, or Firm*—Foley & Lardner

[57] ABSTRACT

The invention relates to storage-stable fibrinogen preparations for preparing concentrated fibrinogen solution for use as a tissue adhesive or for preparing fibrinogen solutions for other uses, for example, for infusion purposes. The fibrinogen preparations are characterized in that (i) the lyophilized preparation comprises a substance improving the solubility of fibrinogen such that the reconstitution time is up to 15 minutes, preferably less than 7 minutes, when dissolving with water at room temperature to a solution with a fibrinogen concentration of at least 70 mg/ml and (ii) the ready-to-use tissue adhesive solution obtained from the preparation forms fibrin clots having physiological fibrin structure after mixing with a thrombin-$CaCl_2$ solution.

25 Claims, No Drawings

STORAGE-STABLE FIBRINOGEN PREPARATIONS

The invention relates to storage-stable fibrinogen preparations for preparing concentrated fibrinogen solutions for use as tissue adhesive or for preparing fibrinogen solutions for other uses, for example for infusion products.

The storage-stable fibrinogen preparations can be present either in lyophilized form or as deep-frozen (especially highly concentrated) fibrinogen solutions and have the advantage that they can be more easily and more quickly reconstituted and liquefied, respectively, than previously known comparable preparations of ready-to-use fibrinogen and/or tissue adhesive solutions.

Further, the invention also comprises the fibrinogen and/or tissue adhesive solutions obtainable from the preparations according to the invention.

Tissue adhesives based on fibrinogen are employed for seamless and/or seam-supporting binding of human or animal tissue or organ parts, for wound sealing, hemostasis and promoting wound healing.

Their mode of action is based on the fact that the (soluble) fibrinogen contained in a ready-to-use, liquid tissue adhesive is converted into (insoluble) fibrin and the Factor XIII also contained therein is activated to Factor XIIIa, by the action of thrombin. This crosslinks the formed fibrin to a high polymer which is essential for the effectiveness of the tissue adhesive. The required thrombin activity can either originate from the tissue (the wound surface) to be adhered or can be added in the form of a thrombin and $Ca^{2+}$ ion-containing solution to the tissue adhesive in the course of the sealing. Tissue adhesives based on fibrinogen are already known from AT-B-359 653, AT-B-359 652 and AT-B-369 990. Aside from fibrinogen and Factor XIII they also contain further proteins such as fibronectin and albumin and optionally antibiotic agents. Tissue adhesives are marketed either in the form of deep-frozen solutions or as a lyophilisate because as a liquid solution they are not very stable over a longer period of time. These circumstances lead to the fact that the commercial products must be either thawed, i.e. liquefied, or reconstituted from their lyophilisate before their application. Both measures are associated with significant efforts.

For optimal adhesion, a concentration of fibrinogen of at least 70 mg/ml of the ready-to-use tissue adhesive solution is required and an amount of Factor XIII is required whereby the ratio of Factor XIII to fibrinogen is at least 80, expressed in units of Factor XIII per gram fibrinogen.

Such preparations permit, in particular, a safe hemostasis, good adherence of the seal to the wound and/or tissue areas, high strength of the adhesions and/or wound sealings, complete resorbability of the adhesive in the course of the wound healing process, and they have wound healing promoting properties.

However, the necessary high fibrinogen concentration results in the fact that the lyophilized and/or deep-frozen fibrinogen preparations are only gradually reconstituted and/or liquefied ("melted") to a ready-to-use, liquid tissue adhesive, and at increased temperature—generally over 25° C., mostly over 30° C.

From a medical standpoint, a quick availability of the ready-to-use tissue adhesive solution is desired because this can be of decisive importance, especially in surgical emergency situations.

Additionally, as little manipulation as possible should be required for the preparation of the ready-to-use solution in order to keep the burden of the assisting personnel in operations as small as possible, and it is also considered to be advantageous if no additional means are required for this.

Further, from a medical standpoint, ready-to-use tissue adhesive solutions are desired which, despite their high fibrinogen content, are already fluid enough to be easily processed at room temperature, i.e. at 20° C.

Relatively fluid tissue adhesive solutions are especially advantageous when the tissue adhesive is introduced by thin catheters to body cavities and should be applied there, or also when applied by the spray technique whereby the tissue adhesive is sprayed and applied as a thin layer to wound surfaces. Suitable application devices for tissue adhesives are already available (EP 0 315 222, EP 0 455 626).

The solubility of fibrinogen preparations of the prior art can be further reduced by employing virus inactivation methods. These are preferably carried out in such a manner that the lyophilized material is subjected to a heat treatment, for example according to EP 0 159 311.

Therefore, many efforts were undertaken to improve the solubility of lyophilized fibrinogen preparations.

It is known that the reconstitution of lyophilisates can be improved by certain additives. Thus, EP-A-0 345 246 describes a lyophilized fibrinogen preparation which, besides fibrinogen, further contains at least one biologically acceptable tenside. The addition of tensides results in an improved wetting of the lyophilisate with the solvent, whereby the rate of dissolution at a certain temperature is improved, but not the solubility of the fibrinogen itself. Therefore, such preparations must also be reconstituted at temperatures over 25° C., preferably at 37° C.

EP-A-085 923 describes a lyophilized fibrinogen preparation which, aside from fibrinogen, further contains a substance which possesses an urea or a guanidine group. However, it has been demonstrated that lyophilized tissue adhesive preparations made accordingly act cytotoxically, inhibit the growth of fibroblasts and lead to an altered, nonphysiological fibrin structure whereby the desired elasticity of fibrin and the seal is lost (see Redl et al., Medizinische Welt 36, 769–76 (1985)). By the inhibition of the fibroblast growth, i.e. those cells which initiate the wound healing process, the desired wound healing promoting properties of tissue adhesives based on fibrinogen are lost. Further, the required high adhesive strength in vivo is jeopardized by the absent elasticity of the resulting fibrin.

Object of the present invention is to provide storage-stable fibrinogen preparations in lyophilized form or a form resulting from deep-freezing liquid preparations (deep-frozen) which can be reconstituted and liquefied quickly and in a simple manner to ready-to-use fibrinogen and/or tissue adhesive solutions—preferably without the use of additional means such as heating and/or stirring devices, wherein the ready-to-use tissue adhesive solutions (with a fibrinogen concentration of at least 70 mg/ml) are already fluid enough in order to be easily processed, and, despite this, do not possess the above-discussed disadvantages of known preparations, especially those corresponding to EP-A-085 923.

The object is solved according to the invention in that the preparations contain, besides fibrinogen and optionally further proteins as well as adjuvants and additives, at least one substance which improves the solubility of the preparations and/or lowers their liquification temperatures and reduces the viscosity of a ready-to-use tissue adhesive solution at room temperature. Thereby, the substances are selected not only according to their effect on the solubility of fibrinogen, but also according to the formation of a physiological fibrin structure when the dissolved preparation reacts with an activator and fibrin clots are formed. This can be proven by mixing the fibrinogen solution with the equal volume of a thrombin-$CaCl_2$ solution (essentially comprising 4 IU thrombin and 20–40 μmol $CaCl_2$/ml), if the formed clots possess a physiological fibrin structure, i.e. the typical, spatial branched fibril structure as they are formed by the action of thrombin on fibrinogen under physiological conditions, i.e. at an ionic strength of approximately 0.15 and a pH value of approximately 7.4. The physiological structure is macroscopically characterized by an opaque and viscoplastic clot. Scanning electron micrographs (SEM) photographs of typical physiological or non-physiological fibrin clots are shown, for example, in the publication of Redl et al., Medizinische Welt 36, 769–76 (1985).

The preparation according to the invention is composed in such a manner that it has no cytotoxic effect when used as a tissue adhesive, i.e. it is very well tolerated by cells, permits a good cell growth and offers an ideal prerequisite for good wound healing therewith. This may be proven by dilution of the tissue adhesive with the equal volume of the half-isotonic or isotonic sodium chloride solution, and no damaging effect on fibroblasts is detectable.

A fibrinogin and/or tissue adhesive solution is generally referred to as non-cytotoxic if it exerts no damaging effect on fibroblasts in the cell topping test according to Redl et al. (see above)

Further, the preparation according to the invention is preferably composed in a way to fulfill all the further demands to a tissue adhesive, namely virus safety, High adhesive strength and/or dressable wound sealings as well as safe and sustained hemostasis, Controllable durability of the adhesions in the body through a variable content of plasminogen and/or fibrinolysis inhibitor, Complete resorbability of the adhesive in the course of the wound healing process and Wound healing promoting properties i.e. that the usually desired biochemical and physical properties of the tissue adhesive are practically not. negatively influenced by the content of a substance of the tissue adhesive according to the invention which improves the solubility of the preparation and/or lowers its liquification temperature and reduces the viscosity of the ready-to-use tissue adhesive at room temperature.

This can be demonstrated by the following further exemplary tests:

Coagulation reaction after mixing with a thrombin solution (coagulation time)

Crosslinking of fibrin-γ and α chains fibrinolysis resistance tensile strength adhesion strength.

Liquification temperature is understood as that temperature at which a deep-frozen concentrated fibrinogen solution is liquefied with increasing temperature.

The storage-stable fibrinogen preparation in fluid-deep-frozen form according to the invention contains a solubility improving substance in a manner that it is liquifiable to a solution with a fibrinogen content of at least 70 mg/ml at a temperature of 0–25° C., preferably below 20° C., particularly preferably below 15° C. A lowered liquification temperature also means a quicker liquification of a deep-frozen, concentrated fibrinogen solution if this is exposed to a surrounding temperature of 20° C.–25° C. (room temperature) for example. This is especially true for the deep-frozen preparations according to the invention which are filled into ready-to-use, sterile disposable syringes and are double sealed in plastic film for reasons of sterility. The heat exchange is more difficult by the necessary double coating, for which reason deep-frozen stored preparations packed in this manner could only be liquefied, i.e. made ready-to-use, in a reasonable time by means of a water bath (37° C.) up to now. However, the use of a water bath is troublesome and associated with handling disadvantages, for example with respect to the maintenance of sterile conditions.

The lyophilized fibrinogen and/or tissue adhesive preparations according to the invention also have the advantage that these can be reconstituted to a solution with a fibrinogen content of at least 70 mg/ml at room temperature without special means (such as for example the combined heating and stirring device according to AT-B-371 719) in a reasonable time, i.e. in a time period of approximately ½ minute up to 15 minutes, preferably less than 7 minutes, particularly preferably less than 5 minutes. Up to now, this was only the case with preparations according to EP-A-085 923; however, these preparations possess serious disadvantages as mentioned above.

Further, the preparations according to the invention also permit particularly quick and easy provision of fibrinogen solutions for other purposes, for example for infusion.

It was surprisingly found that a series of substances fulfill the above-described demands, i.e. increase the solubility of fibrinogen, lower the liquification temperature of concentrated, deep-frozen fibrinogen and/or tissue adhesive solutions as well as their viscosity at room temperature without causing the further above-described undesired side-effects of additives according to EP-A-085 923.

The preparations according to the invention contain one or more of the substances selected from the group of benzene, pyridine, piperidine, pyrimidine, morpholine, pyrrole, imidazole, pyrazole, furan, thiazole, purine compounds or vitamins, nucleic bases, nucleosides or nucleotides, preferably in the amount of 0.03 mmol–3 mmol, most preferred in an amount of 0.07 mmol–1.4 mmol, per g fibrinogen.

For the preparation of infusion solutions from lyophilized fibrinogen preparations, it is advantageous to choose relatively higher ratios of the amount of the substance with respect to fibrinogen. For example, the substance can be present in an amount of 0.12–12 mmol, preferably 0.28–5.6 mmol, per g fibrinogen in an infusion product.

Among these substances are, for example, benzoic acid, p-aminobenzoic acid (vitamin H'), p-aminosalicyclic acid, hydroxybenzoic acid, hydroxysalicyclic phenylalanine, procaine, niacin, niacinamide, picolinic acid, vitamin $B_6$ (pyridoxin), hydroxypyridines, pyridine dicarboxylic acid, pyridine sulfonic acid, piperidine carboxylic acid ester, pyrimidine, barbituric acid, uracil, uridine, uridine phosphate, thymine, cytosine, cytidine, hydroxypyrimidine, thiamine (vitamin $B_1$), morpholine, pyrrolidone, imidazole, histidine, hydantoin, pyrazole dicarboxylic acid, phenazone, adenosine, adenosine phosphate, inosine, guanosine phosphate, α-furoic acid (furan-2-carboxylic acid), ascorbic acid (vitamin C) and xantosine.

The type and amount of the substance is to be selected in such a manner that the ready-to-use tissue adhesive preparation is fluid enough at room temperature in order to be able to be sprayed without a problem, corresponding to a viscosity of less than 400 cSt, preferably less than 300 cSt, and physiological clots are formed after mixing the ready-to-use tissue adhesive solution with a thrombin-$CaCl_2$ solution in the ratio 1:1.

The fibrinogen preparations according to the invention are further characterized by the relatively low salt content such that the osmolarity of the concentrated tissue adhesive solution is preferably less than 500 mOsm, mostly preferred less than 400 mOsm. This limit is necessary in order to permit the desired good cell tolerance (absence of cytotoxic properties). Due to the substances according to the invention, it is now possible to create lyophilized fibrinogen preparations with relatively low salt content which, despite this, can be reconstituted to ready-to-use, relatively fluid tissue adhesive solutions (with a fibrinogen content of at least 70 mg/ml) at room temperature as described above and are tolerated well by cells.

Previously, preparations which have become known are either soluble at room temperature, but cell damaging (Beriplast, Biocol, Bolheal HG-4) or are tolerated well by cells but are only reconstitutable at increased temperature—preferably at 37° C. (Tissucol).

The preparations according to the invention can also be provided as virus-safe preparations due to their composition. They dissolve well even despite pre-treatments for the inactivation or depletion of viruses. Multi-step heat treatment methods, for example steam treatment at 60° C. and 80° C. according to EP 159 311 or also combinations of chemical and/or physical treatment methods are particularly effective treatment methods.

A heat treatment method is performed before the addition of the solubility improving substance to the preparation, and optionally a nanofiltration before filling into the final container.

Preferably, the preparation according to the invention further contains Factor XIII, and optionally fibronectin or small amounts of plasminogen which can be advantageous in the course of wound healing.

On the other hand, in certain cases, a preparation according to the invention can essentially consist of fibrinogen only, i.e. contain fibrinogen as the single active substance.

A further preferred embodiment relates to tissue adhesive based on fibrinogen and a plasminogen activator inhibitor and plasmin inhibitor such as aprotinin, $\alpha_2$-plasmin inhibitor, $\alpha_2$-macroglobulin and the like. The ready-to-use tissue adhesive solution generally contains 70–120 mg fibrinogen, optionally 0.5–50 U Factor XIII, optionally 0.5 to 15 mg fibronectin, 0 to 150 μg plasminogen and 0 to 20,000 KIU aprotinin, preferably 1,000 to 15,000 KIU aprotinin, per ml. A preferred preparation further contains small tenside concentrations for a better wetting of the lyophilized preparation and/or for improvement of the deep-frozen preparations.

The invention is more closely illustrated by the following examples.

EXAMPLE 1

Liquification Temperatures of Different Deep-Frozen Tissue Adhesive Solutions A virus inactivated (steam treated) tissue adhesive preparation was produced as follows according to known methods (see AT-B-369 653, EP 0 345 246):

A plasma cryoprecipitate from pooled human citrated plasma was washed with a buffer solution (pH 6.5) containing 6.6 g sodium citrate.2H$_2$O, 3.4 g NaCl, 10 g glycine, 25,000 KIU aprotinin and 200 I.U. heparin per l at 2° C. and centrifuged. The precipitate was adjusted to a protein concentration of 42 g/l with a further buffer solution containing 9.0 g glycine, 1.0 g sodium citrate.2H$_2$O, 25,000 KIU aprotinin and 0.2 g Triton WR 1339. Then, 4.5 g pure human albumin and 15,000 U Factor XIII were added per liter and the pH value was adjusted to 7.3. The solution was lyophilized in bulk, adjusted to a moisture content of 7.5% and heated under N$_2$ atmosphere for 10 hours at 60° C. The virus-inactivated material thus obtained was dissolved with distilled water to a protein concentration of 47 g/l, sterile filtered and lyophilized again. Portions of the lyophilized material were dissolved in distilled H$_2$O to a fibrinogen concentration of 85 mg/ml with or without the additives given in Table 1 (=ready-to-use tissue adhesive solution), 2 ml each was filled into test tubes and deep-frozen.

The liquification temperature of the deep-frozen tissue adhesive solution obtained in this manner was determined in the following liquification test:

The deep-frozen samples are first incubated in a water bath, kept at a constant temperature of 10° C. for 30 minutes. Thereafter, the temperature is increased in intervals of 30 minutes by 2.5° C. respectively. After each incubation period, the aggregate state of the samples is assessed by tipping the test tube. The transition from solid to liquid state does not occur abruptly, but over a range of several temperature steps, wherein gelatinous and viscous transitory states are passed.

According to this test, a sample is designated as "liquid" not until a horizontal liquid level forms when tipping the test tube, i.e. when the sample does not form a visable bulge immediately upon flowing.

With the aid of this simple test, it can be determined whether a tissue adhesive solution is sufficiently fluid at a given temperature in order to be easily used.

The results are summarized in Table 1.

Additionally, it was investigated whether the mentioned tissue adhesive solution formed physiological, opaque, viscoplastic clots as desired after mixing with the same volume of a thrombin-CaCl$_2$ solution (4 I.U. thrombin and 40 μmol CaCl$_2$ per ml, produced from Thrombin 500, Immuno AG). This was the case with all mentioned tissue adhesive solutions.

TABLE 1

| | Results | | |
|---|---|---|---|
| Added Substance | Group and/or Compound | Concentration mM | Liquification Temperature ° C. |
| no additive (comparative) | — | — | 27.5 |
| benzoic acid (Na-salt) | benzene | 200 | 15 |
| p-aminobenzoic acid (Na-salt) | benzene vitamin | 25 50 | 20 12.5 |
| p-aminosalicylic acid (Na-salt) | benzene | 50 100 | 15 10 |
| p-hydroxybenzoic acid (Na-salt) | benzene | 50 100 | 15 10 |
| phenylalanine | benzene | 100 | 20 |
| procaine•HCl | benzene | 50 | 15 |
| niacin (Na-salt) | pyridine | 50 100 | 22.5 10 |
| niacinamide | pyridine, vitamin | 50 100 200 | 12.5 10 <10 |

TABLE 1-continued

Results

| Added Substance | Group and/or Compound | Concentration mM | Liquification Temperature ° C. |
|---|---|---|---|
| Picolinic acid | pyridine | 50 | 22.5 |
|  |  | 100 | 10–12.5 |
| pyridoxine•HCl adermin, vitamin $B_6$ | pyridine, vitamin | 50 | <10 |
| pyridine-2,6-dicarboxylic acid•Na | pyridine | 50 | 10 |
| 2-hydroxypyridine | pyridine | 50 | 15 |
|  |  | 100 | 12.5 |
| 3-hydroxypyridine | pyridine | 200 | 17.5 |
| 4-hydroxypyridine | pyridine | 50 | 10 |
| pyridine-2,3-carboxylic acid•Na | pyridine | 50 | 17.5–20 |
| pyridine-3-sulfonic acid•Na | pyridine | 50 | 20 |
|  |  | 100 | 15 |
|  |  | 200 | 10 |
| piperidine-4-carboxylic acid ester | piperidine | 100 | 20 |
| pyrimidine | pyrimidine | 50 | 22.5 |
|  |  | 100 | 12.5 |
| barbituric acid•Na | pyrimidine | 50 | 10 |
| uracil | pyrimidine nucleic base | 25 | 22.5 |
| uridine | pyrimidine, nucleoside | 50 | 10 |
| uridine-5'-phosphate | pyrimidine | 25 | 10 |
| thymine | pyrimidine, nucleic base | 25 | 22.5 |
| cytosine | pyrimidine, nucleic base | 25 | 10 |
| cytidine | pyrimidine, nucleotide | 50 | 12.5 |
| 4-hydroxypyrimidine (4,3H-pyrimidone) | pyrimidine | 50 | 10 |
| morpholine | morpholine | 100 | 15 |
| α-pyrrolidone | pyrrole | 50 | 10–12.5 |
|  |  | 100 | 10 |
| imidazole | imidazole | 100 | 17.5 |
|  |  | 200 | 12.5 |
| histidine | imidazole | 50 | 20 |
|  |  | 100 | 12.5 |
| hydantoin | imidazole | 50 | 22.5 |
|  |  | 100 | 10 |
| pyrazole-3,5-dicarboxylic acid | pyrazole | 25 | 12.5 |
| phenazone, antipyrine | pyrazole | 50 | 12.5 |
| adenosine | purine, nucleoside | 25 | 12.5 |
| inosine | purine, nucleoside | 25 | 12.5 |
|  |  | 50 | 10 |
| adenosine-5'-phosphate | purine, nucleotide | 6.25 | 22.5 |
|  |  | 12.5 | 10 |
| guanosine-5'-phosphate | purine, nucleotide | 6.25 | 15 |
|  |  | 12.5 | 10 |
| furan-2-carboxylic acid, α-furoic acid | furan | 100 | 17.5 |
|  |  | 200 | 10 |
| furan-3-carboxylic acid | furan | 100 | 22.5 |
|  |  | 200 | 12.5 |
| ascorbic acid | furan, vitamin | 50 | 15 |
| xanthosine | purine, nucleoside | 25 | 12.5 |
|  |  | 50 | 10 |

EXAMPLE 2

Influence of Niacinamide on the Viscosity of Tissue Adhesive Solutions

Analogously to Example 1, fluid-deep-frozen tissue adhesive solutions (content of coagulable protein: 81 mg/ml) were produced with different contents of niacinamide.

After thawing, the kinematic viscosity at different temperatures was measured in a capillary viscometer.

The results are summarized in Table 2.

Table 2:

Dependence of kinematic viscosity of a tissue adhesive solution on the content of niacinamide at different temperatures:

| Niacin-amide (mM) | Viscosity (cSt) at °C. | | | | | | | | |
|---|---|---|---|---|---|---|---|---|---|
|  | 10.0 | 12.5 | 15.0 | 17.5 | 20.0 | 22.5 | 25.0 | 30.0 | 37.0 |
| 0(comparison) |  |  |  |  | 812 | 432 | 238 | 107 | 58.6 |
| 25 |  |  | 1152 | 531 | 294 | 184 | 92.6 | 54.8 |  |
| 50 |  | 850 | 471 | 277 | 184 | 132 | 81.3 | 52.9 |  |
| 100 |  | 1035 | 556 | 332 | 216 | 152 | 114 | 73.7 | 52.0 |
| 200 | 646 | 424 | 286 | 207 | 152 | 118 | 93.5 | 66.2 |  |

EXAMPLE 3

Influence of Pyrodoxine-HCl on the Viscosity of Tissue Adhesive Solutions

Carried out analogously to Example 2; results Table 3

Table 3:

Dependence of the kinematic viscosity of the tissue adhesive solution on the content of pyridoxine.HCl.

| Pyridoxine-HCl(mM) | Viscosity (cSt) at °C. | | | | | | | |
|---|---|---|---|---|---|---|---|---|
|  | 12.5 | 15.0 | 17.5 | 20.0 | 22.5 | 25.0 | 30.0 | 37.0 |
| 0(comparison) |  |  |  | 812 | 432 | 238 | 107 | 59 |
| 12.5 |  |  |  | 695 | 372 | 214 | 97 | 57 |
| 25 |  |  | 945 | 459 | 252 | 159 | 85 | 51 |
| 50 |  | 1151 | 583 | 323 | 196 | 147 | 85 |  |
| 100 | 803 | 499 | 315 | 215 | 153 | 116 | 63 | 47 |

EXAMPLE 4

Influence of Niacinamide on the Reconstitution Time of Lyophilized Tissue Adhesive Preparations A lyophilized, virus-inactivated tissue adhesive preparation was produced analogously to Example 1 up to the heating step.

Thereafter, the material was dissolved to a protein concentration of 30 g/l with distilled $H_2O$ and/or aqueous niacinamide solutions of different concentration, sterile filtered, filled of portions of 4.0 ml each into sterile final containers (small glass bottles) and lyophilized.

After reconstitution with 1.0 ml $H_2O$ or aqueous aprotinin solution, ready-to-use tissue adhesive solutions were obtained with a fibrinogen content of 85 mg of each variant /ml. The required reconstitution time at room temperature was determined by gentle shaking by hand. Several determinations were done for several small bottles. The results are summarized in Table 4.

Aprotinin up to a concentration of 3,000 KIU/ml in the solvent had no significant influence on the reconstitution time.

Table 4

Reconstitution Times of Lyophilized Tissue Adhesive Preparations as a Function of Content of Niacinamide.

| Niacinamide, Final Concentration (mM) | Reconstitution Time at RT (min.) |
| --- | --- |
| 0 (Comparison) | >20 |
| 50 | 9–11 |
| 100 | 6–8 |
| 200 | 4–5 |

EXAMPLE 5

Cell Compatibility of the Tissue Adhesives According to the Invention

The tissue adhesive preparations from Example 4 were examined as to their cell compatibility according to Redl et al., Med. Welt 36, 769–776, 1985. A known cytotoxic tissue adhesive preparation corresponding to EP-A-0 085 923 served as a negative control.

Results:

All preparations from Example 4 (with a content of niacinamide of up to 200 mmol/l) proved to be well-tolerated by cells. In contrast, the tissue adhesive preparation corresponding to EP-A-0 085 923 led to severe cell damage within a few minutes as expected, whereby the sensitivity of the test system was ensured.

EXAMPLE 6

A purified lyophilized fibrinogen preparation (bulk material) was essentially produced according to L. A. Kazal et al., Proc. Soc. Exp. Biol. Med. 113, 989–994, 1963, by glycine precipitation from a fibrinogen-containing human plasma fraction.

This material was adjusted to a residual moisture of 7–8% and heated for further virus inactivation under $N_2$ atmosphere 10 hours long at 60° C. and thereafter for 3 hours at 80° C.

The result of the analysis of the material was as follows:
Protein 73.0% (g/g)
Coagualable Protein (Fibrinogen) 69.4% (g/g)
$Na_3$-citrate.$2H_2O$ 19.5% (g/g)

Solutions containing 22 g fibrinogen and 10 g human albumin per liter, pH 7.4, with different niacinamide contents were produced from aliquots of this material, and the osmolarity of these solutions was adjusted by addition of NaCl to approximate 300 mOsm.

After sterile filtration, the solutions were filled to 50 ml each in 125 ml bottles and lyophilized.

The lyophilized fibrinogen preparations obtained in this manner were each dissolved with 50 ml $H_2O$ at room temperature under gentle shaking by hand and the reconstitution times were measured. Thereby, the end point was very rigorously defined: A preparation was considered as dissolved not until no more undissolved particles were visible in transparent light. The results (average values from three determinations) are summarized in the following Table.

| Additive | Niacinamide Concentration mmol/l | mmol/g Fibrinogen | Reconstitution Time at RT (min.) |
| --- | --- | --- | --- |
| 0 (Comparison) | 0 | 0 | 21 |
| Niacinamide | 50 | 2.3 | 13 |
| Niacinamide | 100 | 4.5 | 7 |

The example shows the favorable influence of solubility improving substances according to the invention on the dissolubility of heated lyophilized fibrinogen preparations which are formulated to be used as infusion preparations and are about isotonic for optimal compatibility after reconstitution.

EXAMPLE 7

A fibrinogen-containing human plasma fraction was treated with Tween 80 essentially as described in AU-B-18306/92 in order to inactivate viruses, such as HIV, which may be present in human plasma.

After this first virus inactivation step, the material was further purified by glycine precipitation similar to Example 6 and washing of the precipitate obtained with a 25 mM Na-citrate solution, pH 7.3, at 0–2° C.

The purified precipitate was dissolved to yield a solution of 50 g protein and 10 mmol Na-citrate per liter, pH 7.3, and lyophilized.

The lyophilized bulk material obtained was adjusted to a residual moisture of 7–8% and heated for further virus inactivation under $N_2$ atmosphere for 10 hours at 60° C. and thereafter for 1 hour at 80° C.

Thereafter, the material was dissolved at a protein concentration of 40g/l with a solution containing per liter 40 mmol histidine.HCl, 40 mmol niacinamide, 80 mg Tween 80, and 100,000 KIU aprotinin, adjusted to pH 7.3 with NaOH. Virus inactivated human albumin was added at a concentration of 6 g/l, and human purified Factor XIII, virus inactivated according to Austrian Patent Application A 1548/93, was added at a concentration of 15,000 U per liter.

The solution was sterile filtered, filled in portions of 2.5 ml each into sterile final containers (glass bottles) and lyophilized.

Upon reconstitution with 1.0 ml of water or aprotinin solution, a ready-to-use tissue adhesive solution containing per ml 90 mg fibrinogen, 2.5 mg fibronectin, 15 mg albumin, 100 μmol histidine and 100 μmol niacinamide was obtained.

The average reconstitution time at room temperature, determined as in Example 4, was only 4 min.

Example 7 demonstrates that a combination of solubility improving substances according to the invention is particularly effective in providing highly soluble lyophilized tissue adhesive preparations which at the same time have a very high degree of virus safety due to two different and independent virus inactivation steps during manufacture.

I claim:

1. A lyophilized storage-stable fibrinogen preparation, wherein
    (i) the lyophilized storage-stable preparation comprises a substance for improving the solubility of fibrinogen such that reconstitution time is no longer than 15 minutes when dissolving with water at room temperature to form a solution with a fibrinogen concentration of at least 70 mg/ml, wherein the substances improving the solubility of fibrinogen is at least one selected from the group consisting of:
    vitamins,
    nucleic bases, nucleosides and nucleotides,
    piperidine, pyrimidine, morpholine, pyrrole, imidazole, pyrazole, furan, thiazole and purine, benzoic acid, p-aminobenzoic acid (vitamin H'), p-aminosalicyclic acid, hydroxybenzoic acid, hydroxysalicyclic acid, hydroxypyridines, pyridine dicarboxylic acids, and pyridinesulfonic acid; and wherein
    (ii) a tissue adhesive solution obtained from the lyophilized storage-stable preparation forms fibrin clots having physiological fibrin structure after mixing with a solution comprising thrombin and CaCl$_2$.

2. A deep-frozen storage-stable fibrinogen preparation in, wherein
(i) the deep-frozen preparation comprises a substance for improving the solubility of fibrinogen such that the preparation is liquifiable to a solution having a fibrinogen concentration of at least 70 mg/ml at a temperature of 0 to 25° C., wherein the substance improving the solubility of fibrinogen is at least one selected from the group consisting of:
vitamins,
nucleic bases, nucleosides and nucleotides,
piperidine, pyrimidine, morpholine, pyrrole, imidazole, pyrazole, furan, thiazole and purine, benzoic acid, p-aminobenzoic acid, (vitamin H'), p-aminosalicyclic acid, hydroxybenzoic acid, hydroxysalicyclic acid, hydroxypyridines, pyridine dicarboxylic acids, and pyridinesulfonic acid; and wherein
(ii) a tissue adhesive solution obtained from the lyophilized storage-stable preparation forms fibrin clots having physiological fibrin structure after mixing with a solution comprising thrombin and CaCl$_2$.

3. A preparation according to claim 1, wherein the substance improving the solubility of fibrinogen has no cytotoxic effect at the selected concentrations in the preparation.

4. A lyophilized storage-stable fibrinogen preparation, wherein
(i) the preparation comprises a substance improving the solubility of fibrinogen in order that the reconstitution time is no longer than 15 minutes when dissolving with water at room temperature to form a solution having a fibrinogen concentration of at least 70 mg/ml, wherein said substance improving the solubility of fibrinogen is selected from the group consisting of phenylalanine, procaine, niacin, niacinamide, picolinic acid, vitamin B$_6$ (pyridoxine), piperidine carboxylic acid ester, pyrimidine, barbituric acid, uracil, uridine, uridine phosphates, thymine, cytosine, cytidine, hydroxypyrimidines, thiamine (vitamin B$_1$), morpholine, pyrrolidone, imidazol, histidine, hydantoin, pyrazole dicarboxylic acid, phenazone, adenosine, adenosine phosphates, inosine, guanosine phosphates, α-furoic acid (furan-2-carboxylic acid), ascorbic acid (vitamin C) and xantosine, and
(ii) the tissue adhesive solution obtained from the preparation forms fibrin clots having physiological fibrin structure after mixing with a thrombin-CaCl$_2$ solution.

5. A preparation according to claim 1, wherein the substance is present in an amount of from 0.03 to 3 mmol per gram fibrinogen.

6. A preparation according to claim 1, wherein the tissue adhesive solution forms an opaque and viscoelastic fibrin clot in no more than 10 minutes at 37° C. after mixing with an equal volume of a solution comprising 4 IU thrombin and 40 μmol CaCl$_2$ per ml.

7. A preparation according to claim 1, wherein the tissue adhesive solution has no cytotoxic effect.

8. A preparation according to claim 1, wherein no fibroblast damage is detectable after dilution of the tissue adhesive solution with the equal volume of an isotonic sodium chloride solution.

9. A lyophilized fibrinogen preparation containing a substance for improving the solubility of fibrinogen, wherein the substance is at least one selected from the group consisting of benzoic acid, p-aminobenzoic acid, (vitamin H'), p-aminosalicyclic acid, hydroxybenzoic acid, hydroxysalicyclic acid, hydroxypyridines, pyridine dicarboxylic acids, pyridinesulfonic acid, piperidine, pyrimidine, morpholine, pyrrole, imidazole, pyrazole, furan, thiazole and purine, wherein the substance has no cytotoxic effect at the concentration present in the preparation.

10. A lyophilized fibrinogen preparation comprising at least one vitamin for improving the solubility of fibrinogen.

11. A lyophilized fibrinogen preparation comprising at least one substance selected from the soup consisting of nucleic bases, nucleosides and nucleotides, wherein the substance improves the solubility of fibrinogen.

12. A lyophilized fibrinogen preparation comprising a substance for improving the solubility of fibrinogen, wherein the substance for improving the solubility of fibrinogen is selected from the group consisting of benzoic acid, phenylalanine, procaine, niacin, niacinamide, picolinic acid, vitamin B$_6$ (pyridoxine), piperidine carboxylic acid ester, pyrimidine, barbituric acid, uracil, uridine, uridine phosphates, thymine, cytosine, cytidine, hydroxypyrimidines, thiamine (vitamin B$_1$) morpholine, pyrrolidone, imidazol, histidine, hydantoin, pyrazole dicarboxylic acid, phenazone, adenosine, adenosine phosphates, inosine, guanosine phosphates, α-furoic acid (furan-2-carboxylic acid), ascorbic acid (vitamin C) and xantosine.

13. A fibrinogen preparation according to claim 9, wherein the substance is in an amount of 0.12–12 mmol/g fibrinogen.

14. A fibrinogen preparation according to claim 9, wherein the substance is in an amount of 0.28–5.6 mmol/g fibrinogen.

15. A lyophilized fibrinogen preparation comprising fibrinogen and a compound for improving the solubility of fibrinogen, wherein the compound is at least one selected from the group consisting of benzoic acid, p-aminobenzoic acid (vitamin H'), p-aminosalicyclic acid, hydroxybenzoic acid, hydroxysalicyclic acid, hydroxypyridines, pyridine dicarboxylic acids, pyridinesulfonic acid, piperidine, pyrimidine, morpholine, pyrrole, imidazole, pyrazole, furan, thiazole, vitamins purine, nucleic bases, nucleosides and nucleotides.

16. A preparation comprising a compound for improving the solubility of fibrinogen, wherein the compound is at least one selected from the group consisting of benzoic acid, phenylalanine, procaine, niacin, niacinamide, picolinic acid, vitamin B$_6$ (pyridoxine), piperidine carboxylic acid ester, pyrimidine, barbituric acid, uracil, uridine, uridine phosphates, thymine, cytosine, cytidine, hydroxypyrimidines, thiamine (vitamin B$_1$), morpholine, pyrrolidone, imidazol, histidine, hydantoin, pyrazole dicarboxylic acid, phenazone, adenosine, adenosine phosphates, inosine, guanosine phosphates, α-furoic acid (furan-2-carboxylic acid), ascorbic acid (vitamin C) and xantosine.

17. A preparation according to claim 15, wherein the compound is present in an amount of 0.03 to 3 mmol per gram fibrinogen.

18. A preparation according to claim 17, wherein the compound is present in an amount of 0.7 to 1.4 mmol per gram fibrinogen.

19. A frozen fibrinogen preparation comprising fibrinogen and a compound for improving the solubility of fibrinogen fibrinogen, wherein the compound is at least one selected from the group consisting of benzene, pyridine, piperidine, pyrimidine, morpholine, pyrrole, imidazole, pyrazole, furan, thiazole, vitamins, purine nucleic bases, nucleosides and nucleotides.

20. A frozen fibrinogen preparation comprising a compound for improving the solubility of fibrinogen, wherein the compound is at least one selected from the group consisting of benzoic acid, phenylalanine, procaine, niacin, niacinamide, picolinic acid, vitamin $B_6$ (pyridoxine), piperidine carboxylic acid ester, pyrimidine, barbituric acid, uracil, uridine, uridine phosphates, thymine, cytosine, cytidine, hydroxypyrimidines, thiamine (vitamin $B_1$), morpholine, pyrrolidone, imidazol, histidine, hydantoin, pyrazole dicarboxylic acid, phenazone, adenosine, adenosine phosphates, inosine, guanosine phosphates, à-furoic acid (firan-2-carboxylic acid), ascorbic acid (vitamin C) and xantosine.

21. A preparation according to claim 19, wherein the compound is present in an amount of 0.03 to 3 mmol per gram fibrinogen.

22. A preparation according to claim 21, wherein the compound is present in an amount of 0.7 to 1.4 mmol per gram fibrinogen.

23. A storage-stable fibrinogen preparation according to claim 1, wherein the reconstitution time is less than 7 minutes.

24. A storage-stable fibrinogen preparation according to claim 5, wherein the substance is contained in an amount of from 0.7 to 1.4 mmol per gram fibrinogen.

25. A storage-stable fibrinogen preparation according to claim 2, wherein the temperature is below 20° C.

\* \* \* \* \*